US00PP22102P2

(12) United States Plant Patent
Saul

(10) Patent No.: US PP22,102 P2
(45) Date of Patent: Aug. 30, 2011

(54) ***ECHINACEA* PLANT NAMED 'GEMINI PINK'**

(50) Latin Name: ***Echinacea purpurea*×*Echinacea paradoxa***
Varietal Denomination: Gemini Pink

(75) Inventor: Richard Gregg Saul, Cleveland, GA (US)

(73) Assignee: ITSAUL Plants, Alpharetta, GA (US)

( * ) Notice: Subject to any disclaimer, the term of this patent is extended or adjusted under 35 U.S.C. 154(b) by 0 days.

(21) Appl. No.: 12/807,630

(22) Filed: Sep. 9, 2010

(51) Int. Cl.
*A01H 5/00* (2006.01)

(52) U.S. Cl. ..... Plt./428

(58) Field of Classification Search ..... Plt./428
See application file for complete search history.

*Primary Examiner* — Kent L Bell
(74) *Attorney, Agent, or Firm* — C. A. Whealy

(57) ABSTRACT

A new and distinct cultivar of *Echinacea* plant named 'Gemini Pink', characterized by its upright, outwardly spreading and mounding plant habit; vigorous growth habit; freely branching habit; dense and bushy habit; freely flowering habit; fragrant inflorescences with numerous red purple-colored ray florets; strong flowering stems that hold the inflorescences upright; and good garden performance.

2 Drawing Sheets

Botanical designation: *Echinacea purpurea*×*Echinacea paradoxa.*

Cultivar denomination: 'GEMINI PINK'.

BACKGROUND OF THE INVENTION

The present invention relates to a new and distinct cultivar of *Echinacea* plant, botanically known as *Echinacea purpurea*×*Echinacea paradoxa* and hereinafter referred to by the name 'Gemini Pink'.

The new *Echinacea* is a product of a planned breeding program conducted by the Inventor in Dahlonega, Ga. The objective of the breeding program is to create new *Echinacea* plants with double whorls of ray florets and unique and attractive ray and disc floret coloration.

The new *Echinacea* plant originated from an open-pollination during the summer of 2007 of an unnamed selection of *Echinacea purpurea*×*Echinacea paradoxa* which had double whorls of ray florets, not patented, as the female, or seed parent with an unknown selection of *Echinacea purpurea*× *Echinacea paradoxa* as the male, or pollen, parent. The new *Echinacea* plant was discovered and selected by the Inventor as a single flowering plant from within the progeny of the stated open-pollination grown in a controlled outdoor nursery environment in Dahlonega, Ga. in June, 2008.

Asexual reproduction of the new *Echinacea* plant by tissue culture in a controlled environment in Alpharetta, Ga. since 2008 has shown that the unique features of this new *Echinacea* plant are stable and reproduced true to type in successive generations.

SUMMARY OF THE INVENTION

Plants of the new *Echinacea* have not been observed under all possible environmental conditions. The phenotype may vary somewhat with variations in environment such as temperature and light intensity, without, however, any variance in genotype.

The following traits have been repeatedly observed and are determined to be the unique characteristics of 'Gemini Pink'.

These characteristics in combination distinguish 'Gemini Pink' as a new and distinct cultivar of *Echinacea:*

1. Upright, outwardly spreading and mounding plant habit.
2. Vigorous growth habit.
3. Freely branching habit; dense and bushy habit.
4. Freely flowering habit.
5. Fragrant inflorescences with numerous red purple-colored ray florets.
6. Strong flowering stems that hold the inflorescences upright.
7. Good garden performance.

Plants of the new *Echinacea* differ from plants of the female parent selection in the following characteristics:

1. Plants of the new *Echinacea* and the female parent selection differ in leaf color.
2. Inflorescences of plants of the new *Echinacea* have more ray florets than inflorescences of plants of the female parent selection.

Plants of the new *Echinacea* can be compared to plants of *Echinacea purpurea* 'Evan Saul', disclosed in U.S. Plant Pat. No. 17,659. In side-by-side comparisons conducted in Dahlonega, Ga., plants of the new *Echinacea* differed from plants of 'Evan Saul' in the following characteristics:

1. Plants of the new *Echinacea* were taller than plants of 'Evan Saul'.
2. Plants of the new *Echinacea* had larger inflorescences than plants of 'Evan Saul'.
3. Inflorescences of plants of the new *Echinacea* had more ray florets than inflorescences of plants of 'Evan Saul'.
4. Plants of the new *Echinacea* and 'Evan Saul' differed in ray floret color as plants of 'Evan Saul' had orange-colored ray florets.

Plants of the new *Echinacea* can also be compared to plants of *Echinacea purpurea* 'Katie Saul', disclosed in U.S. Plant Pat. No. 18,783. In side-by-side comparisons conducted in Dahlonega, Ga., plants of the new *Echinacea* differed from plants of 'Katie Saul' in the following characteristics:

1. Plants of the new *Echinacea* were bushier and had stronger stems than plants of 'Katie Saul'.

2. Plants of the new *Echinacea* had smaller inflorescences than plants of 'Katie Saul'.
3. Inflorescences of plants of the new *Echinacea* had more ray florets than inflorescences of plants of 'Katie Saul'.
4. Plants of the new *Echinacea* and 'Katie Saul' differed in ray floret color as plants of 'Katie Saul' had salmon pink-colored ray florets.

BRIEF DESCRIPTION OF THE PHOTOGRAPHS

The accompanying photographs illustrate the overall appearance of the new *Echinacea* plant. The photographs show the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet comprises a side perspective view of a typical flowering plant of 'Gemini Pink' grown in a container.

The photograph on the second sheet is a close-up view of typical inflorescences of 'Gemini Pink'.

DETAILED BOTANICAL DESCRIPTION

The aforementioned photographs and following observations and measurements describe plants grown during the summer in 17-cm containers in an outdoor nursery in Alpharetta, Ga. and under conditions and practices which approximate those generally used in commercial *Echinacea* production. During the production of the plants, day temperatures averaged 27° C. and night temperatures averaged 18° C. Plants were one year old when the photographs and description were taken. In the following description, color references are made to The Royal Horticultural Society Colour Chart, 2007 Edition, except where general terms of ordinary dictionary significance are used.

Botanical classification: *Echinacea purpurea*×*Echinacea paradoxa* 'Gemini Pink'.

Parentage:

*Female, or seed, parent.*—Unnamed selection of *Echinacea purpurea*×*Echinacea paradoxa,* not patented.

*Male, or pollen, parent.*—Unknown selection of *Echinacea purpurea*×*Echinacea paradoxa,* not patented.

Propagation:

*Type.*—By tissue culture.

*Time to initiate roots.*—About 15 days at 20° C. to 23° C.

*Time to produce a rooted young plant, summer.*—About six weeks at 26° C.

*Time to produce a rooted young plant, winter.*—About eight weeks at 21° C.

*Root description.*—Fleshy, medium in thickness; white in color.

*Rooting habit.*—Freely branching; moderately dense.

Plant description:

*Plant form/growth habit.*—Upright, outwardly spreading and mounding plant habit; freely basal branching habit with numerous lateral branches; dense and bushy habit; terminal and axillary inflorescences potentially developing at every node and are held upright on strong peduncles; vigorous growth habit.

*Plant height.*—About 35 cm.

*Plant diameter or spread.*—About 41 cm.

*Basal branches.*—Length: About 29 cm. Diameter: About 5 mm. Internode length: About 2.25 cm. Aspect: Mostly upright to slightly outwardly. Strength: Strong. Texture: Longitudinally ridged; towards the base, smooth; towards the apex, pubescent. Color: Close to 144A; older stems overlain with close to 187A.

Foliage description:

*Arrangement.*—Alternate, simple.

*Length.*—About 10 cm.

*Width.*—About 4.5 cm.

*Shape.*—Elliptical.

*Apex.*—Elongate acute.

*Base.*—Attenuate, slightly cordate or truncate.

*Margin.*—Shallow serrations.

*Texture, upper and lower surfaces.*—Sparsely pubescent; rough.

*Venation pattern.*—Pinnate; reticulate.

*Color.*—Developing and fully expanded leaves, upper surface: Darker than 147A; venation, close to 147B. Developing and fully expanded leaves, lower surface: More green than 147B; lateral veins, close to 147B; midvein, close to 147C.

*Petiole.*—Length: About 6 cm. Diameter: About 3 mm. Texture, upper and lower surfaces: Smooth, glabrous. Color, upper and lower surfaces: Centers, close to 147B to 147C; towards the margins, close to 147A.

Inflorescence description:

*Appearance.*—Rotate single inflorescence form with ray and disc florets; inflorescences terminal or axillary; inflorescences potentially developing at every node with about one to two open inflorescences per lateral branch at one time; inflorescences held upright on strong peduncles.

*Fragrance.*—Moderate; sweet, pleasant.

*Time to flower.*—Plants flower continuously from the spring throughout the summer in Georgia.

*Inflorescence longevity.*—Depending on temperature, inflorescences maintain good substance for about two to four weeks on the plant; as a cut flower, inflorescences maintain good substance for about two weeks; inflorescences persistent.

*Inflorescence bud.*—Height: About 1.4 cm. Diameter: About 1.4 cm. Shape: Ovoid. Color: Close to 147A.

*Inflorescence size.*—Diameter: About 6 cm. Depth (height): About 2.75 cm. Disc diameter: About 2.5 cm. Receptacle height: About 1.5 cm. Receptacle diameter: About 7.5 mm. Receptacle shape: Conical.

*Ray florets.*—Length: About 2.6 cm. Width: About 7 mm. Shape: Lanceolate. Apex: Acute or praemorse. Base: Attenuate; fused into a short corolla tube. Texture, upper and lower surfaces: Smooth, glabrous; satiny. Number of ray florets per inflorescence: About 26 arranged in one to two whorls. Aspect: Initially upright to outwardly arching; slightly concave to flat. Color: When opening and fully opened, upper surface: Close to 61A; color becoming closer to 68A with development. When opening and fully opened, lower surface: Close to 64A; color becoming closer to 68B with development.

*Disc florets.*—Shape: Tubular; apex five-pointed. Length: About 6 mm. Diameter: About 1.5 mm. Number of disc florets per inflorescence: Numerous. Texture: Smooth, glabrous. Color: Towards the apex, close to 61A; towards the base, close to 144A.

*Receptacle spines.*—Quantity: One per disc floret. Length: About 1.2 cm. Width: About 2 mm. Shape: Lanceolate to acicular. Apex: Sharply acute. Base: Tapering. Texture: Smooth, glabrous. Color: Apex: Close to 187A. Mid-section: Close to 144A. Base: Close to NN155D.

*Phyllaries.*—Quantity per inflorescence: About 60 in about three to four whorls. Length: About 7 mm. Width: About 3 mm. Shape: Lanceolate. Apex: Acute. Base: Truncate. Margin: Entire. Texture, upper and lower surfaces: Smooth, glabrous. Color, upper and lower surfaces: Close to 147A.

*Peduncles.*—Length, terminal peduncle: About 6.5 cm. Length, uppermost axillary peduncle: About 5.3 cm. Diameter: About 3 mm. Angle, terminal peduncles: Erect. Angle, axillary peduncles: About 20° to 30° from vertical. Strength: Strong. Texture: Smooth, glabrous. Color: Close to 146A.

*Reproductive organs.*—Androecium: Stamens per disc floret: One. Filament length: About 6 mm. Filament color: Close to 145D. Anther shape: Oblong. Anther length: Less than 1 mm. Anther color: Close to 146C. Pollen amount: Scarce. Pollen color: Close to 21A. Gynoecium: Pistil length: About 6 mm. Stigma shape: Bi-parted; reflexed. Stigma color: Close to 187A. Style length: About 5 mm. Style color: Close to 150D. Ovary color: Close to 157A. Seeds/fruits: Seed and fruit development have not been observed on plants of the new *Echinacea.*

Disease/pest resistance: Plants of the new *Echinacea* have not been shown to be resistant to pathogens and pests common to *Echinacea.*

Garden performance: Plants of the new *Echinacea* have been observed to have good garden performance and to tolerate rain, wind and temperatures ranging from about −16° C. to about 37° C.

It is claimed:

1. A new and distinct *Echinacea* plant named 'Gemini Pink' as illustrated and described.

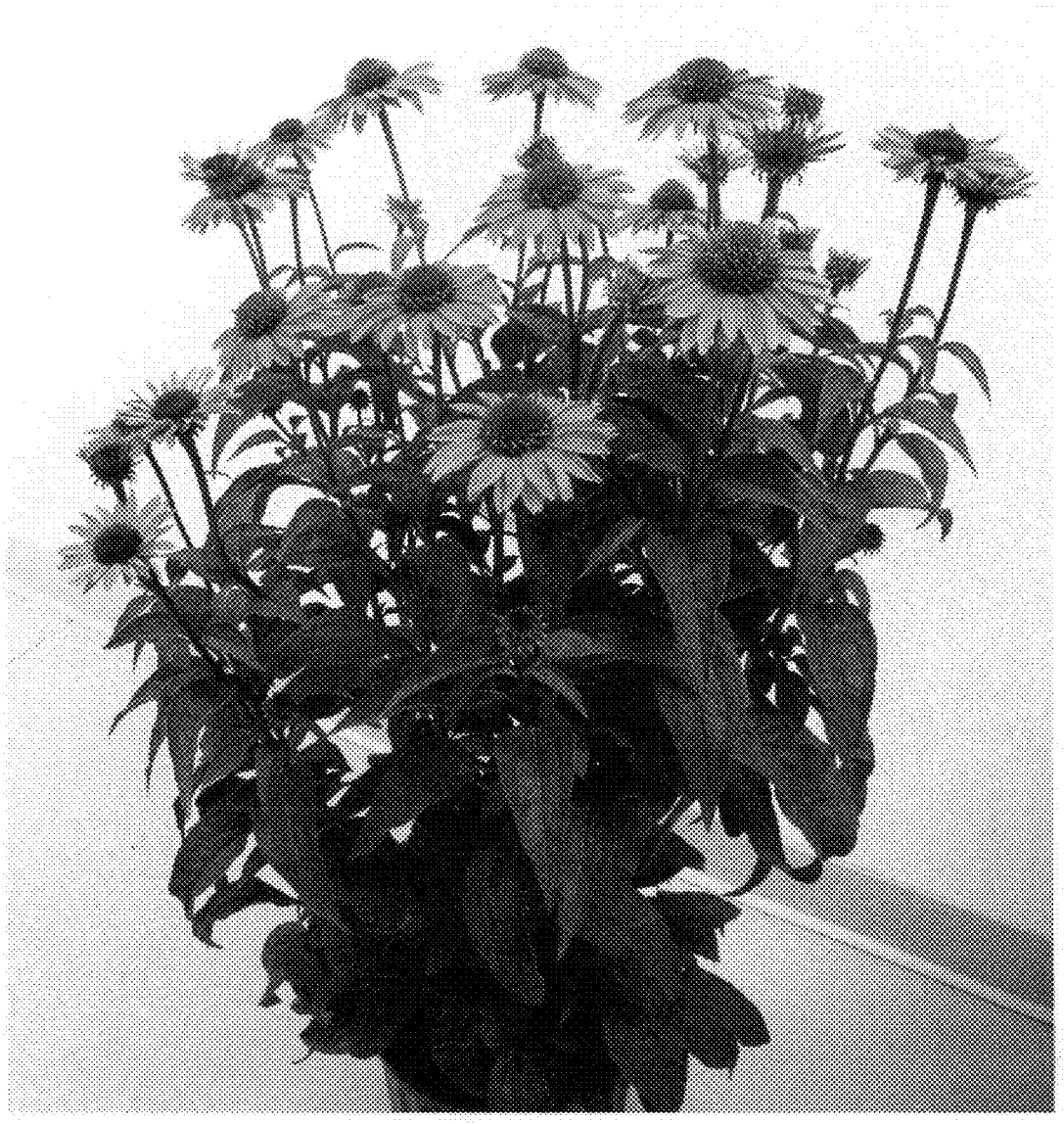

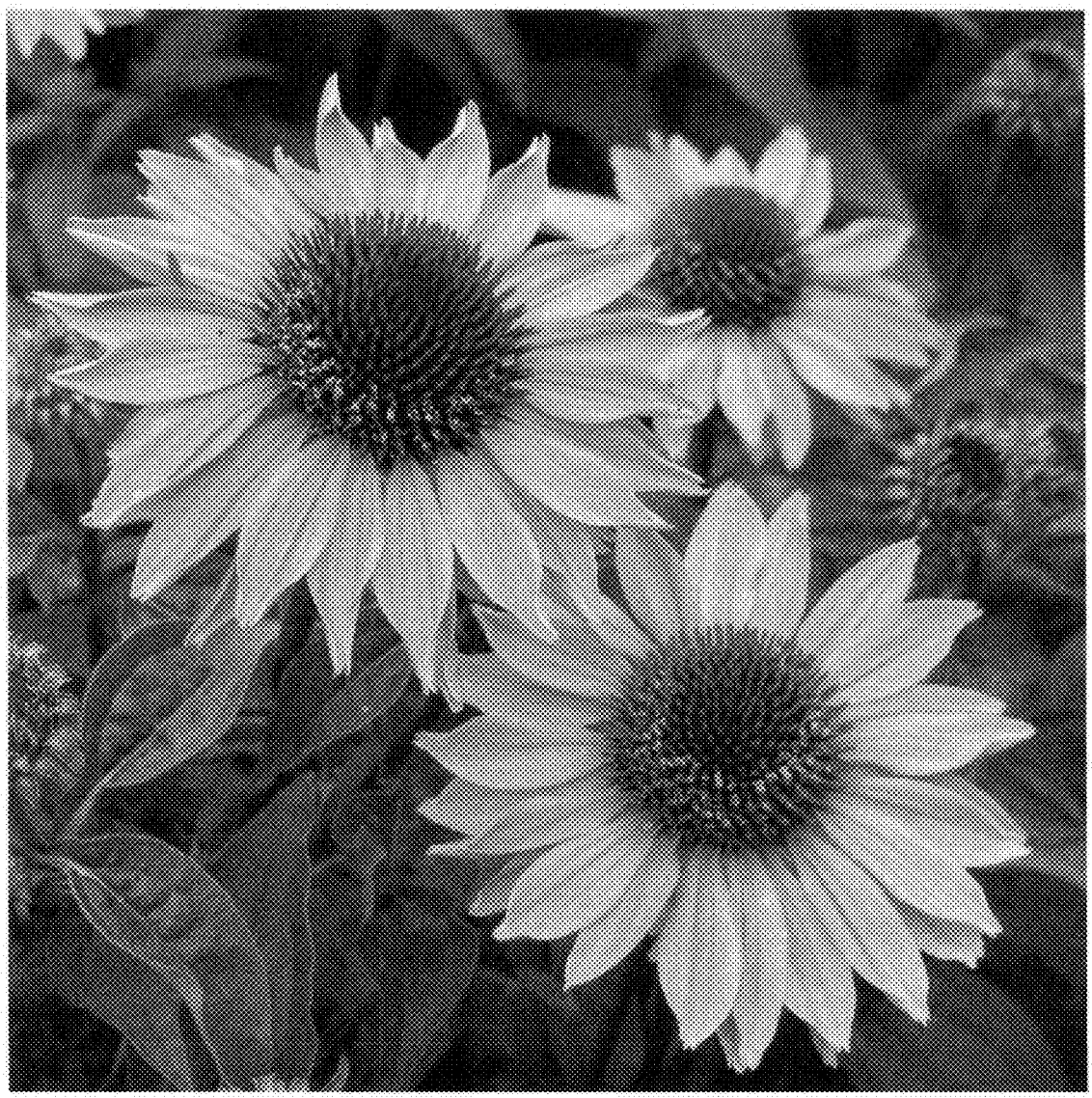

* * * * *